United States Patent [19]

Bowman et al.

[11] 4,325,715

[45] Apr. 20, 1982

[54] APPARATUS FOR DEGASSING HEMODIALYSIS LIQUID

[76] Inventors: Donald B. Bowman, 7635 NW. McDonald Cir.; Charles J. Filz; James G. Osborn, both of 1930 SE. Stone St., all of Corvallis, Oreg. 97330

[21] Appl. No.: 669,903

[22] Filed: Mar. 24, 1976

[51] Int. Cl.³ .................. B01D 19/00; B01D 31/00
[52] U.S. Cl. .................................. 55/158; 55/159; 210/321.3
[58] Field of Search ............... 55/16, 36, 158, 150; 210/22 A, 321 B, 433 M, 500 M, DIG. 5

[56] References Cited
U.S. PATENT DOCUMENTS 2,525,154 10/1950 Taylor .................... 210/DIG. 5
3,463,615 8/1969 Sochor ...................... 55/36 X
3,778,971 12/1973 Granger et al. ............. 55/159
3,794,468 2/1974 Leonard .................... 55/158 X
3,920,556 11/1975 Bowman .................... 210/321 B Primary Examiner—Robert H. Spitzer

[57] ABSTRACT

A coil of hydrophobic tubing is wrapped around the side wall of an inner chamber. The gas-containing hemodialysis liquid is delivered into the inner chamber through one end thereof and flows out from the inner chamber into one end of the hydrophobic tubing through an opening at the opposite end of the inner chamber. It then flows through the tubing back towards the first end of the inner chamber, generally countercurrent to flow through the inner chamber. Gases are released from the liquid through the hydrophobic material into an annular chamber surrounding the tubing.

3 Claims, 4 Drawing Figures

APPARATUS FOR DEGASSING HEMODIALYSIS LIQUID

BACKGROUND OF THE INVENTION

1. Cross-Reference to Related Application

This application is related to my prior U.S. application Ser. No. 479,998, filed June 17, 1974 entitled Hemodialysis System, and now U.S. Pat. No. 3,920,556, granted Nov. 18, 1975. Specifically, the subject matter of this application supersedes the apparatus for removing gas bubbles from the hemodialysis solution disclosed by such patent.

2. Field of the Invention

This invention relates to apparatus for removing gases from liquids, and more particularly, it relates to apparatus for degassing a hemodialysis liquid.

3. Description of the Prior Art

My prior U.S. Pat. No. 3,515,275, granted Jan. 2, 1970, the several patents mentioned therein, and the prior art that was cited and considered by the Patent Office and listed at the end of the patent should be consulted for the purpose of properly evaluating the subject invention and putting it into proper perspective. The following additional patents relating to artificial kidneys or hemodialysis systems, should also be consulted: U.S. Pat. No. 3,352,779, granted Nov. 14, 1967, to Avery J. Austin and Robert S. Patch; U.S. Pat. No. 3,406,826, granted Oct. 22, 1968, to Charles B. Willock; U.S. Pat. No. 3,528,550, granted Sep. 15, 1970, to Christian Cappelen, Jr.; U.S. Pat. No. 3,598,727, granted Aug. 10, 1971, to Charles B. Willock; and U.S. Pat. No. 3,827,561, granted Aug. 6, 1974, to Earl J. Serfass, Edward R. Lindsay, Jr., Gene M. Holmes, James D. Aid and French Bishop, Jr. Several of these patents are concerned with the problems of removing gases from the hemodialysis solution prior to introduction of such solution into the hemodialyzer.

The present invention relates to novel ways of utilizing a hydrophobic material for efficiently removing the unwanted air and other gases.

Additonal United States patents which should be studied in conjunction with the subject invention, some of which involve the use of hydrophobic material, are: U.S. Pat. No. 3,463,615, granted Aug. 26, 1969, to Cestmir Sochor; U.S. Pat. No. 3,492,793, granted Feb. 3, 1970, to Pravin G. Bhuta and Robert L. Johnson; U.S. Pat. No. 3,523,408, granted Aug.11, 1970, to David Rosenberg; U.S. Pat. No. 3,614,856, granted Oct. 26, 1971, to Manuel C. Sanz and John J. J. Staunton; U.S. Pat. No. 3,651,616, granted Mar. 28, 1972, to Alain Blanchard and Alphonse Faure; U.S. Pat. No. 3,665,680, granted May 30, 1972, to Gustav Heuser and U.S. Pat. No. 3,768,563, granted Oct. 30, 1973, to Robert C. Brumfield.

SUMMARY OF THE INVENTION

As explained in Column 2 of the aforementioned U.S. Pat No. 3,523,408, a hydrophobic material is defined as a filter material that is not wetted by liquid and normally remains open for passage of gas. Normally the air or gas flows through such material and the liquid does not and it is in this manner that the air or gas is separated from the liquid.

According an aspect of the invention, an elongated length of hydrophobic tubing is coiled around the side wall means of an inner chamber. The gas-containing hemodialysis liquid is delivered into the inner chamber and then flows therefrom into one end of the tubing. An annular second chamber is provided around the tubing and is connected to a vacuum means. As the liquid flows through the tubing the gases leave it by flowing out through the wall of the tubing into the surrounding chamber. The liquid continues to flow through the tubing and by the time it reaches the second end of the tubing it is sufficiently degassed to be introducible into the hemodialyzer.

Preferably, flow through the tubing is generally counter-current to flow through the inner chamber. This arrangement is advantageous because it results in heat transfer from the relatively warm gas-containing hemodialysis liquid which flows through the inner chamber and the relatively cooler solution that flows through the tubing.

An important feature of the invention is that degassification is effectively achieved without the necessity of heating the hemodialysis solution above the body temperature in order to coalesce dissolved air into bubbles. Also, no separate bubble trap is required. The degasser functions as its own bubble trap.

These and other objects, features, advantages and characteristics of my invention will be better understood from the following detailed description of the preferred embodiment, with reference being made to the accompanying drawing.

DETAILED DESCRIPTION OF THE DRAWING

In the drawing like reference characters refer to like parts, and:

DESCRIPTION OF THE PREFERRED EMBODIMENT

Figure 1:
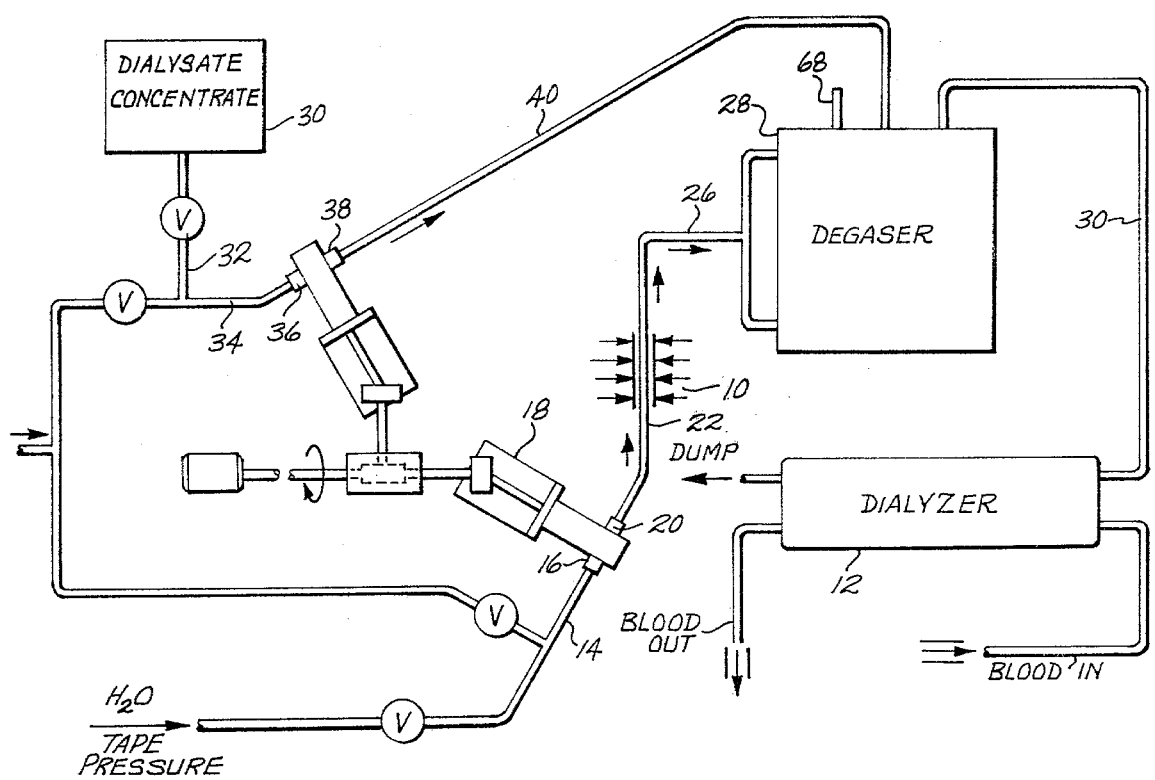
FIG. 1 is a flow diagram of a hemodialysis system employing degassing apparatus according to this invention.

FIG. 1 is a flow diagram of an artificial kidney or hemodialysis system of a type that is particularly suited for home use, and which includes an embodiment of the present invention.

Referring to FIG. 1, a stream of cold water (e.g. cold tap water) is directed through a conduit 14 leading to the inlet 16 of a first positive displacement pump 18. The outlet 20 of pump 18 is connected to a conduit 22 which carries the water to a flow-through heater 10 in which it is heated to a proper temperature for its use in the dialyzer 12. Preferably, the water flows from heater 10 through a conduit 26 into the degassing apparatus 28.

A second pump 27 is used to pump the dialysate concentrate from a reservoir 30 through conduits 32, 34 to a pump inlet 36, and out through the pump outlet 38 into a conduit 40 which leads into the degassing apparatus 28.

As will become evident, the water and concentrate become mixed together in the degassing apparatus 28. A typical ratio of water to dialysate concentrate is 35:1, and as explained in U.S. Pat. No. 3,920,556, the proportioning function is performed by the pumps 18, 27. The degassing apparatus 28 functions to remove unwanted air and other gases from the solution. The degassed solution then flows from degasser 28 through line 30 in which it is subjected to the usual monitors (not shown), then into and through the hemodialyzer 12. In the hemodialyzer 12 the solution passes along one side of semi-permeable membranes in counter flow to the patient's blood which is flowing on the opposite side of the membrane. The cleansed blood is returned to the patient and the spent hemodialysis solution is dumped.

Figure 4:
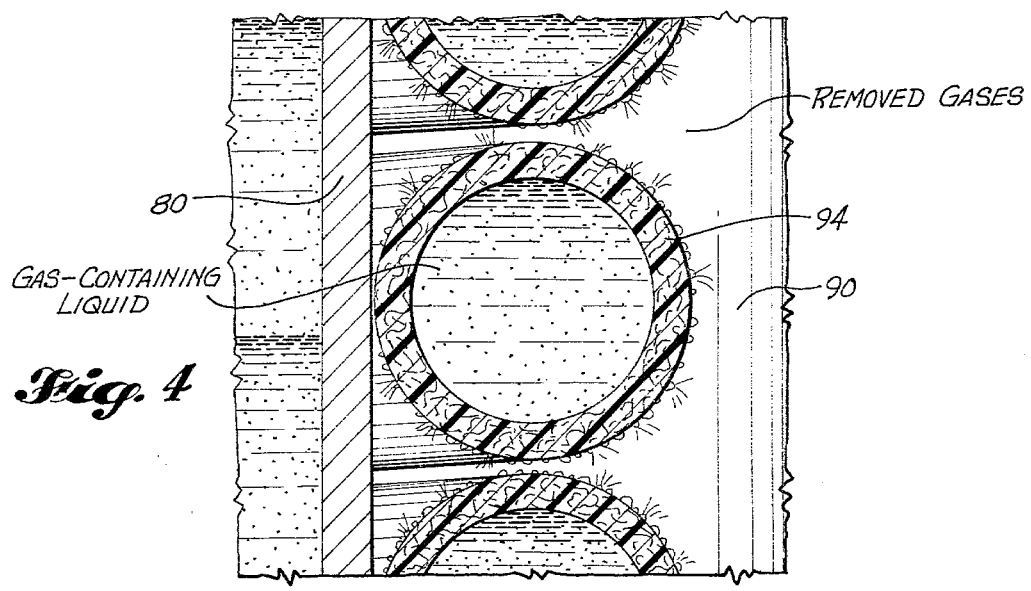
FIG. 4 is an enlarged scale cross-sectional view of a portion of the tubular coil used in the embodiment of FIGS. 2 and 3.

In the illustrated embodiment the liquid is water. However, it is within the scope of the invention for the water and concentrate to be mixed upstream of the degassing apparatus, with the resulting solution being the liquid. In the illustrated embodiment the wall of hydrophobic material is in the form of a plurality of coils 50 of hydrophobic tubing. A pair of headers or manifolds 52, 54 are spaced apart within housing 42, 44, 46. As best shown by FIG. 4, each header 52 (or 54) is provided with a short delivery duct 56 for connection to one end of each coil 50 (i.e. a duct 56 for each coil). Exteriorly, each delivery duct 56 may be formed to include alternating ridge and valley portions 58, 60. A mounting end portion 62 of a coil 50 is stretched over each delivery tube 56. A tubular retainer 64 may be provided around each end portion 62 and heat shrunk to conform it in shape to the exterior configuration of the delivery tube 56.

Figure 2:
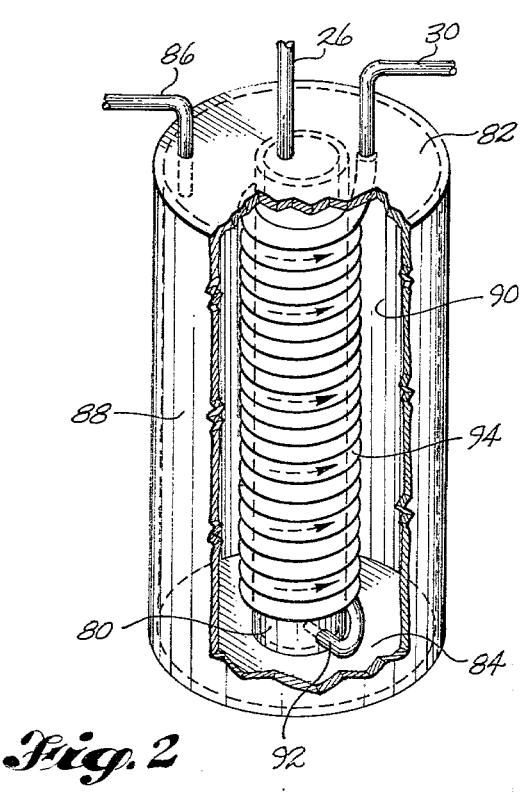
FIG. 2 is a pictorial view, with a foreground portion cut away, showing an embodiment of an apparatus for removing dissolved gases from a hemodialysis solution.
Figure 3:
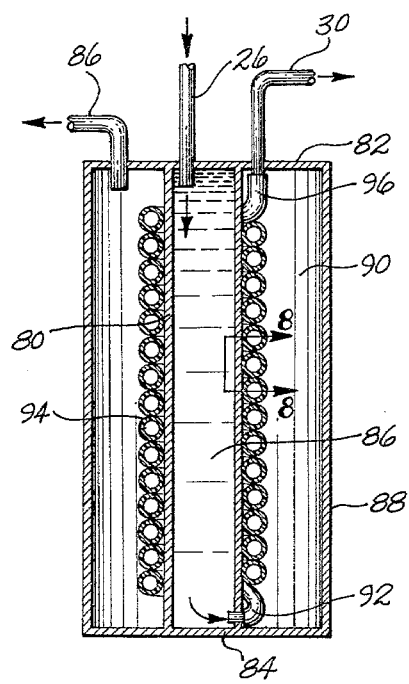
FIG. 3 is an axial sectional view of the apparatus shown in FIG. 2.

Referring now to FIGS. 2-4, and embodiment of the invention comprises wall means 80, 82, 84 defining an inner chamber 86, and wall means 88 forming, in conjunction with wall means 80, 82, 84, and annular outer chamber 90. In this embodiment, the conduit 26 delivers the gas-containing homodialysis solution into the inner chamber 86, preferably through one end thereof. The solution then flows out through the chamber 86, preferably through an outlet at the opposite end thereof, into an inlet end portion 92 of a coil 94 of hydrophobic tubing which is wrapped around the wall means 80. The opposite or outlet end portion 96 of tubing 94 is connected to the conduit 30 leading to the dialyzer 12.

The hydrophobic material, i.e. it passes gases but not water. The gas-containing solution flows into and through chamber 86 and then into and through the tubing 94. The annular outer chamber 90 is connected to a vacuum pump (not shown), such as by means of a tube 86. The subatmospheric pressure on the outside of the tubing wall results in gases only flowing through the wall material. It was found that in operation of this embodiment the air readily come out of its dissolved or mixed state and passes through the pores of the tubing. By the time the liquid reaches conduit 30 a sufficient amount of the gases have been removed so that the liquid could be safely introduced into the dialyzer 12.

Location of the inlet to chamber 86 at one end of the apparatus and the outlet at the other end, and the directional arrangement of the coil 94 on the wall means 80, results in a generally counterflow relationship between the solution flowing through inner chamber 86 and the solution flowing through tubing 94.

It is desirable to prevent any substantial drop in temperature in and about the coil of tubing in order to hold condensation inside the air passageways (i.e. the pores of the hydrophobic material) to a minimum. This is necessary in order to facilitate full passage of air through the wall of the tubing while at the same time retaining the liquid inside the tubing. Some cooling is experienced in the fluid as it flows through the degassing apparatus. The counterflow arrangement provides an advantageous heat exchange between the relatively warmer incoming fluid and the relatively cooler outflowing fluid.

The coil 94 may include a stiff wire (not shown) skeleton for holding their shapes. The wire is stiff enough that when it is wound into a helical coil it maintains that form and in turn maintains the tubing in a helical coil form. The wire may be molding into a wall portion of the tubing material, or may even be inserted into the passageway of the tubing and then formed into a coil. By way of typical and therefor non-limitative example, the coil 94 may be formed from "Goretex", a Trademark product of W. L. Gore & Associates, of Flagstaff, Ariz. "Goretex" comes in a coil form and includes a helical wire skeleton of the type described.

It is to be understood that the invention may be embodied in other specific forms of apparatus without departing from the spirit or basic characteristics of the invention. The illustrated and above described embodiments are to be considered in all respects as illustrative and not restrictive. The scope of the invention is to be determined by the appended claims rather than by the drawing and foregoing description. It is intended that all changes, modifications and/or adaptations which come within the meaning and range of equivalency of the claims are to be considered a part of the invention.

What is claimed is:

1. Apparatus for removing gases from a hemodialysis liquid prior to introduction of such liquid into a hemodialyzer, comprising:

first wall means forming an inner fluid chamber having an inlet for receiving said gas-containing hemodialysis liquid;

second wall means forming, in conjunction with said first wall means, an outer fluid chamber surrounding said inner fluid chamber;

an enlongated length of tubing coiled around said first wall means, with one end of said tubing being in fluid receiving communication with said inner fluid chamber, said tubing being formed from a filter material that is not wetted by liquid and includes pores which normally remain open for passage of gas;

outlet means for degassed hemodialysis liquid connected to the second end of said tubing; and a gas outlet leading outwardly from said outer chamber, for exhausting released gases therefrom.

2. Apparatus according to claim 1, further comprising vacuum means connected to said gas outlet for facilitating gas passage through the wall of said tubing into the outer chamber.

3. Apparatus according to claim 1, wherein the inlet for said inner fluid chamber is at one end thereof and the end of the tubing in fluid receiving communication with said inner fluid chamber is connected to the opposite end of said inner chamber, so that flow through said coil is generally countercurrent to flow through said inner chamber.

* * * * *